(12) United States Patent
Gomez et al.

(10) Patent No.: US 12,042,169 B2
(45) Date of Patent: Jul. 23, 2024

(54) DOUBLE NEEDLE SYSTEM TO FACILITATE PLACING ABDOMINAL WALL NERVE BLOCKS OR INFUSION CATHETERS

(71) Applicant: New Wave Endo-Surgery Inc., Coconut Creek, FL (US)

(72) Inventors: Ricardo Alexander Gomez, Lighthouse, FL (US); Sandy Lawrence Heck, Los Angeles, CA (US)

(73) Assignee: NEW WAVE ENDO-SURGICAL CORP., Coconut Creek, FL (US)

(*) Notice: Subject to any disclaimer, the term of this patent is extended or adjusted under 35 U.S.C. 154(b) by 906 days.

(21) Appl. No.: 16/658,761

(22) Filed: Oct. 21, 2019

(65) Prior Publication Data
US 2020/0121357 A1 Apr. 23, 2020

Related U.S. Application Data

(60) Provisional application No. 62/748,515, filed on Oct. 21, 2018.

(51) Int. Cl.
*A61B 17/34* (2006.01)
*A61B 1/313* (2006.01)
*A61B 17/00* (2006.01)

(52) U.S. Cl.
CPC ........ *A61B 17/3415* (2013.01); *A61B 1/3132* (2013.01); *A61B 17/00234* (2013.01); *A61B 17/3403* (2013.01); *A61B 2017/00283* (2013.01); *A61B 2017/3411* (2013.01)

(58) Field of Classification Search
CPC .......... A61B 17/3415; A61B 17/00234; A61B 17/3403; A61B 1/3132; A61B 2017/00283; A61B 2017/3411
See application file for complete search history.

(56) References Cited

U.S. PATENT DOCUMENTS

| | | | | |
|---|---|---|---|---|
| 6,042,539 | A * | 3/2000 | Harper | A61B 90/50 600/201 |
| 2010/0022974 | A1* | 1/2010 | Sharratt | A61M 5/19 206/570 |
| 2013/0072754 | A1* | 3/2013 | Okamoto | A61B 17/3478 600/114 |
| 2014/0025039 | A1* | 1/2014 | Rajendran | A61M 19/00 604/512 |
| 2015/0231388 | A1* | 8/2015 | Barker | A61N 1/0504 607/116 |
| 2016/0317621 | A1* | 11/2016 | Bright | A61B 90/30 |
| 2020/0170672 | A1* | 6/2020 | Einarsson | A61B 1/00096 |

* cited by examiner

*Primary Examiner* — Brooke Labranche
(74) *Attorney, Agent, or Firm* — GROGAN, TUCCILLO & VANDERLEEDEN, LLP

(57) ABSTRACT

The invention relates to laparoscopic surgery and procedures designed to minimize and numb the pain associated with laparoscopic surgery, including how to locate the target nerve plane, such as the rectus abdominis sheath and transversus abdominus plane. Specialized single and dual needle devices are used. This is accomplished by applying an analgesic to the rectus abdominal sheath or the transversus abdominus plane. More particularly, the invention relates to a pain reduction means using an analgesic delivering device used in laparoscopic surgery. A specialized probe is used to find the correct position and a specialized guide system to speed up the positioning process.

9 Claims, 5 Drawing Sheets

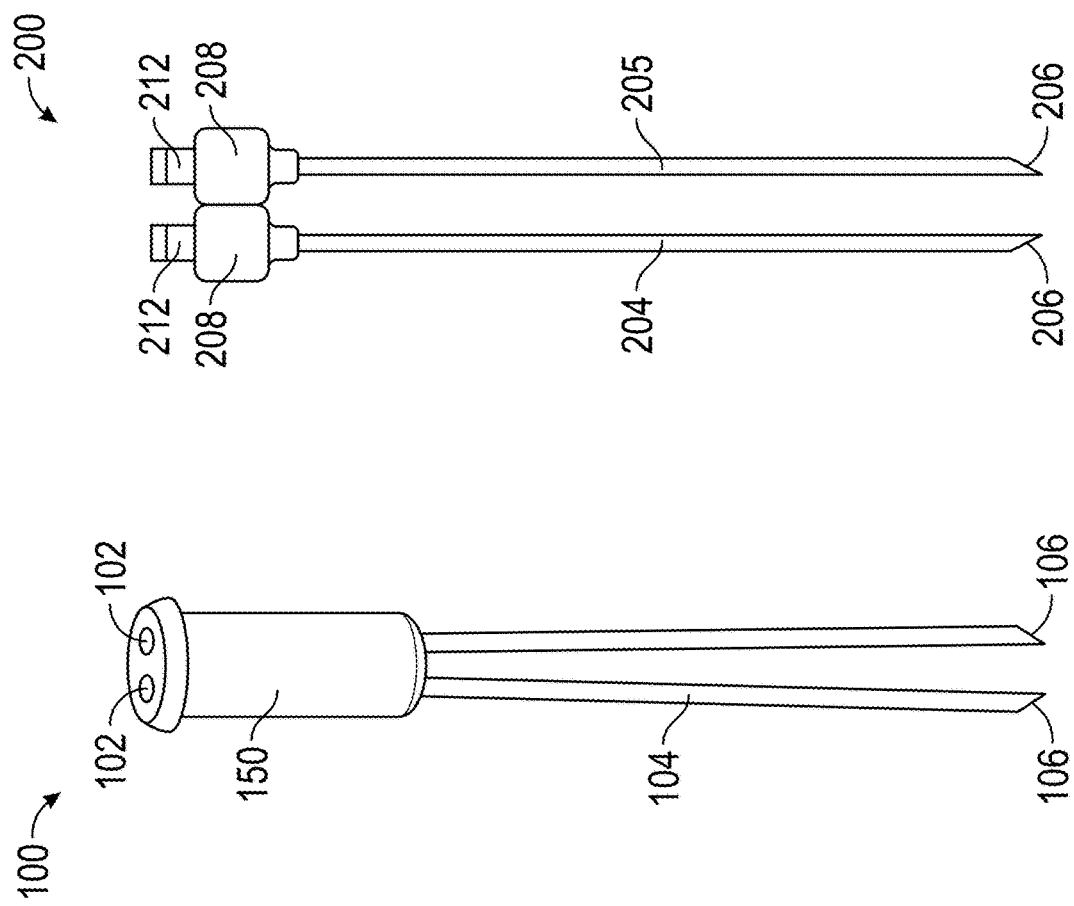
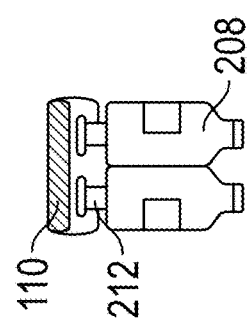
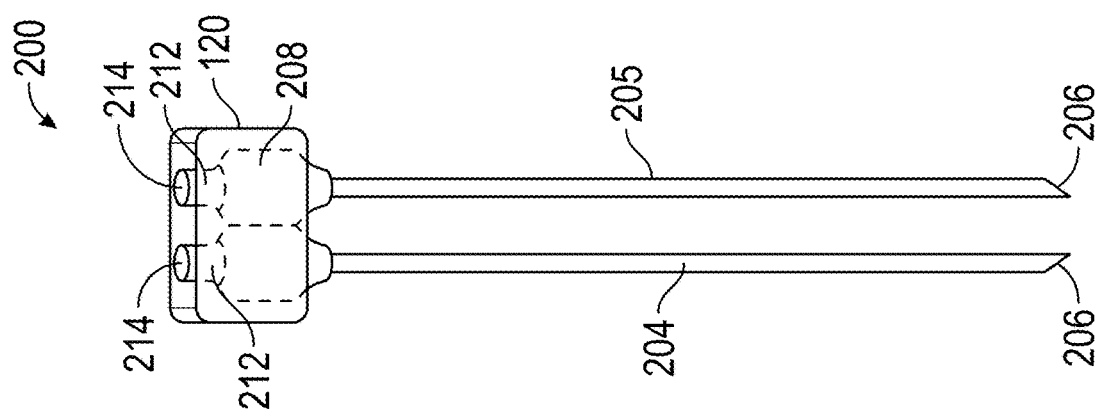

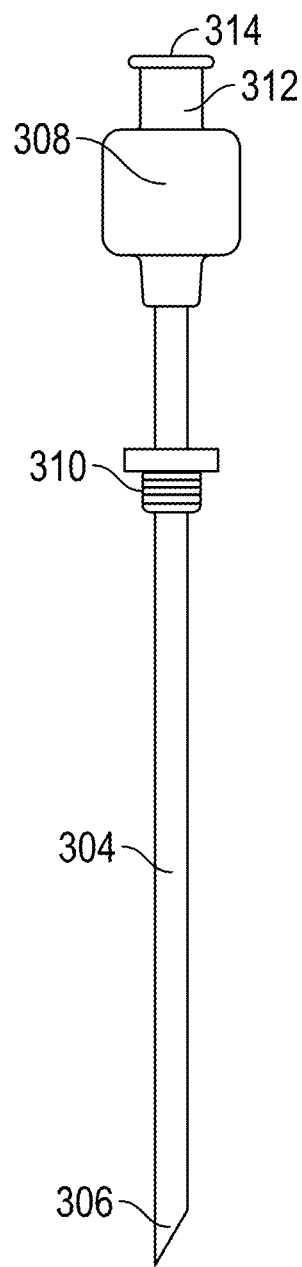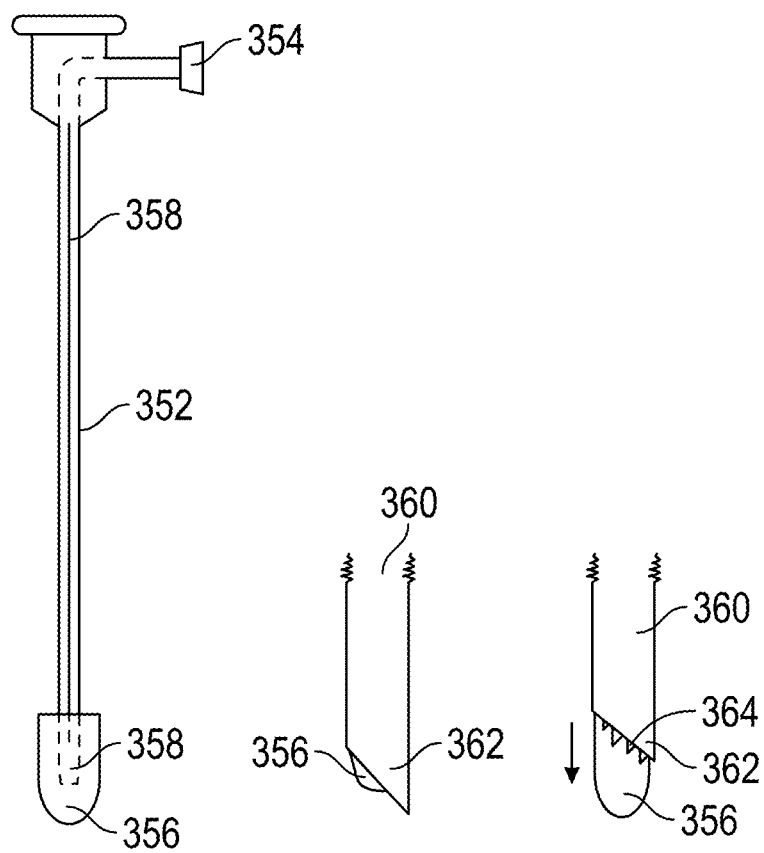
FIG. 2A  FIG. 2B  FIG. 2C  FIG. 2D

DOUBLE NEEDLE SYSTEM TO FACILITATE PLACING ABDOMINAL WALL NERVE BLOCKS OR INFUSION CATHETERS

CROSS-REFERENCE TO RELATED APPLICATIONS

This application claims the priority benefit of U.S. Provisional Patent Application No. 62/748,515 filed on Oct. 21, 2018, titled "Double Needle System to Facilitate Placing Rectus Blocks or Infusion Catheters"," naming the same inventors, and is hereby incorporated by reference for all that is disclosed as though fully set forth herein.

FIELD OF THE INVENTION

The present invention relates to laparoscopic surgery and, in particular, to systems and methods and devices for providing a rectus sheath block, a rectus tap, abdominal wall blocks and infusions using catheters.

BACKGROUND OF THE INVENTION

The human abdominal wall is a complex composite structure having various layers which vary depending on specific anatomical location. The central abdominal wall is composed of the following layers: skin, subcutaneous fat, anterior rectus sheath, rectus abdominis muscle or linea alba, posterior rectus sheath, preperitoneal fat, and peritoneum.

The rectus abdominal muscles are often referred to as the abs. The origin for the term rectus abdominis is from the Latin words rectus, which means straight, and abdominis, indicating that its fibers run in a straight vertical line through the abdominal region of the body. The rectus abdominus muscles are paired parallel muscles, separated by a midline band of connective tissue called the linea alba. The umbilicus, commonly referred to as the belly button, forms part of the linea alba. Its main purpose is to provide a means of sustenance and nutrient flow from the mother into the baby while in her womb. It lies between the two planes and completely seals after birth.

The main function of the rectus abdominis muscle is to provide a means of moving the body between the ribcage and the pelvis. The rectus abdominis muscles are connected at the anterior (top) and posterior (bottom) positions. When the abdominal muscles contract they cause the back to bend. Breathing in, and holding the rectus abdominis in, pulls in the abdomen.

Surgical procedures such as laparotomies and laparoscopies are often used to gain access into the abdominal cavity. Any type of abdominal surgery can be painful and, as such, various procedures have been developed to minimize and numb the pain associated with such surgeries. This can be accomplished by applying a nerve block to the abdominal wall, such as, for example, a rectus abdominal sheath block or a transversus abdominis plane (TAP) block. The rectus abdominal muscles are the main muscles used when laparoscopic rectus abdominis blocks are performed. In contrast, when surgeons refer to a laparoscopic TAP they are typically referring to a transverses abdominal plane. Other blocks in the abdominal wall include preperitoneal nerve blocks, among others.

In a rectus abdominal sheath block (RASB) (also referred to as a rectus sheath block (RSB)), the abdominal muscles are specifically anesthetized through the rectus sheath. The rectus sheath is a thin plane that lies just outside the rectus abdominus muscle. When anesthetized, it numbs the abdominal area. In particular, when a Rectus Sheath Block (RSB) is performed it involves the injection of a local anesthetic between the rectus abdominis muscle and the posterior area. It is used to anesthetize the anterior rami (area) of the T7 to T11 area. The rectus sheath block (RSB) is effective for the postoperative analgesia of midline incision pain such as that following an open abdominal surgery or cesarean delivery. The rectus sheath block was first described by Dr Carl Ludwig Schleich in 1899 as a means of facilitating surgery involving the anterior (top) abdominal wall in adults.

Anesthetization can be performed by a surgeon or anesthesiologist, but often requires special training. Traditionally, a rectus sheath block is performed via a blind technique using the loss of resistance felt as the blunt or block needle is advanced through the fascial and muscle planes. This technique has, however, remained underused primarily due to concerns about the accuracy of the needle placement, particularly in relation to the underlying peritoneal structures. Ultrasonography-guided rectus sheath blocks offer significant advantages, such as providing noninvasive imaging of the anatomy, facilitating real-time needle guidance, and allowing observation of the local anesthetic spread within the correct tissue plane. A recent systematic review of ultrasonography-guided truncal blocks strongly recommended the use of ultrasonographic guidance for rectus sheath block in order to increase its success rate. Even though studies, to date, back the statistical power to demonstrate any safety advantage conferred with the use of ultrasonography, the visualization of real-time sonography, especially with in-plane techniques, are likely to reduce the incidence of inadvertent needle entry into the peritoneum, blood vessel or bowel, and increase the rate of successful nerve blocks.

In connection with the above, the rectus abdominis muscles are unique in that the right side of the muscle is in very close proximity of the left side muscle. Applying rectus sheath blocks requires practice because they are typically done one side at a time. Accordingly, it takes great skill to do one side, let alone having to repeat it again on the other side. The practice and skill needed to successfully and consistently perform such procedure, is one of the main reasons rectus sheath blocks are not more popular.

A transversus abdominis plane (TAP) block is a peripheral nerve block which anesthetizes the abdominal wall. Compelling data continues to emerge showing the benefits of post-operative pain management by using a rectus sheath block with a catheter. The catheter allows the patient to self-administer pain medication, which is desirable because substantial evidence confirms that when a patient has control of self-medicating they tend to use less pain medication.

Compared to the transversus abdominis plane block, the rectus sheath block appears to provide a denser analgesia but of a shorter duration. Thus, the rectus sheath block is only useful for prolonged postoperative analgesia if continuous catheters are placed with regular dosing of local anesthetics into the posterior rectus sheath. It has been suggested that continuous indwelling rectus sheath catheter placement possesses several advantages over epidural catheter placement, which is commonly performed for postoperative analgesia. Continuous rectus sheath block also offers the major advantage of mobility. It combines excellent analgesia with preservation of limb strength and no mandatory connection to infusion devices, thus allowing patients to regain mobility early. Moreover, the rectus sheath catheter can be safely inserted under general anesthesia, avoiding patient discomfort and distress, which can occur during epidural insertion in an awake patient. This potentially increases patient acceptance of undergoing rectus sheath block.

To improve the adoption of this clinically superior treatment, ways of facilitating the bilateral nerve blocks, particularly rectus sheath block, are critical. In view of the above, therefore, there is a need for a system, apparatus and method that enables a surgeon or anesthesiologist to quickly, easily, and accurately deliver an analgesic to the rectus sheath plane or transversus abdominus plane.

SUMMARY OF THE INVENTION

The present invention relates to a laparoscopic analgesic delivery system comprising a more accurate means of placing the analgesic drug into the rectus abdominis plane, the transversus abdominis plane (TAP), or other nerve plane in the abdominal wall. A novel single or double needle stylet is used via a guide system to position the delivery system at the appropriate depth of the respective planes. One of the guide systems incorporates a special illuminating probe having a sharp distal end that holds a movable LED. The LED is used to position the distal end just before piercing the peritoneum. As the light source gets closer to the peritoneum the user can determine just how close they want to get without puncturing into the body cavity. At this point the LED is extended causing the circular shaped LED to act as a blunt device and prevent puncturing the cavity. A small amount of analgesic can also leak out around the edge of the exposed LED. The lighted source uses a fiber optics cable to deliver the light at the distal end of the probe device. This lighted source can be powered by batteries or an external power source. Once the proper plane is reached, the LED can be retracted and the analgesic allowed to saturate the plane. The illuminated probe can be of a portable configuration. Once the desired depth is achieved a depth blocking device is lowered to the skin preventing the needle device from accidently going too far.

The present invention also includes a needle guide system which can be configured for single needle or double needle usage. At its circular center is a hole that permits proper orientation by positioning the hole above the umbilicus. Also, a suction valve may be used to fasten the guide device to the skin surface by creating a vacuum seal. Other methods of attachment can be used including, not limited to but including using an adhesive. A fulcrum located in the guide device interior underneath the openings changes the angle of the stylets or needles to the proper insertion angle.

The invention incorporates the use of catheters for attachment to the needle device that allows the user to self-medicate. A dual needle device is unique in that it allows the rectus abdominus muscles to be anesthetized simultaneously. The fact that dual plungers are used with a flat top clip permits the miniature catheter to be connected to a tubing to evenly administer an analgesic to both sides of the rectus abdominis sheath. Tubing with connectors are used to connect to the needles and to an analgesic source which could be but not limited to an injection.

The novelty in using the specialized needles with a guide device which is not limited to but may include a sonogram device or other specialized locating device with or without a monitor is that the Rectus Sheath and Transversus Abdominis Plane can be located quickly and is much simpler to use which allows users to learn quickly and provides a means of self-medicating.

Other aspects and advantages of the present invention will become apparent from the following detailed description, which when taken in conjunction with the accompanying drawings illustrates by way of example the principles of the invention.

BRIEF DESCRIPTION OF DRAWINGS

The preferred embodiments of the invention will hereinafter be described in conjunction with the appended drawings provided to illustrate and not to limit the invention, in which:

FIG. 1A is a side elevational view of a system/device for delivering analgesic to the abdominal wall, according to an embodiment of the present invention.

FIG. 1B is a side elevational view of a system/device for delivering analgesic to the abdominal wall, according to another embodiment of the present invention.

FIG. 1C is an enlarged, side elevational view of a portion of the system/device of FIG. 1B, illustrating a cap for simultaneous dispensing of the contents of individual reservoirs.

FIG. 1D is a side elevational view of the system/device of FIG. 1B, illustrating a cap for simultaneous dispensing of the contents of individual reservoirs according to another embodiment of the invention.

FIG. 2A is a side elevational view of a system/device for delivering analgesic to the abdominal wall, according to another embodiment of the invention.

FIG. 2B is a side elevational view of an optical guide device forming a part of a system for delivering analgesic to the abdominal wall.

FIG. 2C is an enlarged, detail view of a distal end of the guide device of FIG. 2B, showing an LED in a recessed position within an outer cannula stylet.

FIG. 2D is an enlarged, detail view of a distal end of the guide device of FIG. 2B, showing an LED in an exposed position within the outer cannula stylet.

DETAILED DESCRIPTION OF THE INVENTION

Figure 3A:
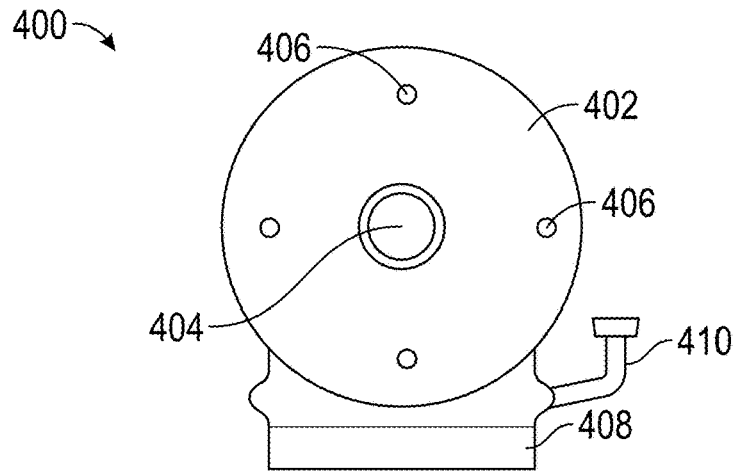
FIG. 3A is a top, plan view of a stylet guide device for use with, for example, the single stylet device of FIG. 2A.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

With respect to FIG. 1A, a surgical device (100) for delivering analgesic to the abdominal wall of a patient is illustrated. The device (100) includes a generally cylindrical hub (150) having at a pair (i.e., two) ports (102) in a top surface thereof, and a pair of hollow needles or cannula stylets (104) that extend from the hub (150) opposite the ports (102). The cannula stylets (104) each have hollow interior passageways that are in fluid communication with a corresponding port (102) via the hub (150). As illustrated in FIG. 1A, each of the cannula stylets (104) is formed with a tapered or sharp distal end defining a piercing tip (106) for piercing the skin of a patient. As indicated above, importantly, the two cannula stylets (104) are connected to a common hub (150). The ports (102) in the hub (150) are utilized to inject an analgesic into the device (100) for delivery to a predetermined abdominal plane through the cannula stylets (104) once the piercing tips (106) of the stylets are positioned in the desired location. For example, a syringe or similar reservoir containing analgesic can be connected or coupled to the ports for injecting the analgesic through the ports. In an embodiment, the device (100) may be utilized to deliver an analgesic to, for example, the rectus abdominus plane and/or the transversus abdominus plane.

Turning now to FIG. 1B, a surgical device (200) for delivering analgesic to the abdominal wall of a patient, according to another embodiment of the invention, is illustrated. As shown therein, the device (200) includes first and second cannula stylets (204, 205), each having a sharp piercing tip (206) at respective distal ends thereof, and each having a reservoir (208) at respective proximal ends thereof. The cannula stylets (204, 205) each have hollow interior passageways that are in fluid communication with the corresponding reservoir (208), respectively. The reservoirs (208) are each configured to contain a predetermined amount of analgesic for delivery to a patient. As illustrated in FIG. 1B, each reservoir (208) includes a plunger (212) that can be actuated or depressed to dispense the contents of each reservoir (208) through the cannula stylets (204, 205). In contrast to the device (100) of FIG. 1A, the device (200) essentially includes two separate cannulas and reservoirs that are joined together at the reservoirs (208). In an embodiment, the reservoirs (208) may be joined together by an adhesive, using mechanical means, or may be integrally formed (but maintaining separation between the contents of the two reservoirs (208)). In use, the plungers (212) may be depressed simultaneously to simultaneously dispense the contents of the reservoirs (208) through the respective cannula stylets (204, 205). Alternatively, the plungers (212) may also be depressed individually (i.e., not simultaneously) to deliver the contents of the reservoirs (208) through the respective cannula stylets (204, 205) at different times.

Turning now to FIG. 1C, in an embodiment, the device (200) may include a cap or clip (110) that is configured to be received atop the adjacent plungers (212) to enable simultaneous dispensing of the contents of each reservoir (208). In particular, the cap (110) includes a substantially planar underside surface that is configured to contact the upper surface of each plunger (212) so that pressing downward on the cap (110) (i.e., on the top surface thereof) causes a downward force to be simultaneously and evenly exhibited on the plungers (212). In an embodiment, the cap (110) may be selectively attachable to, and removable from, the device (200).

FIG. 1D illustrates an alternative configuration of a cap (120) for the device (200) that enables simultaneous dispensing of the contents of each reservoir (208), as well as the selective introduction of additional analgesic, medications, etc. As shown therein, the cap (120) is operatively connected to the plungers (212) such that depression of the cap (120) effects a corresponding, and simultaneous, downward movement each plunger (212), causing the contents of each reservoir (208) to be simultaneously dispensed through each cannula stylet (204, 205). As also illustrated in FIG. 1D, in an embodiment, the device (200) may include a pair of ports (214) or passages that extend through the cap (210) and which provide respective passageways to each reservoir (208). As will be appreciated, this allows additional analgesic, medications, etc. to be loaded into the reservoirs (208) and delivered through the cannula stylets (204, 205) (such as by connecting a syringe, etc. to one or both ports). Importantly, this allows an analgesic to be delivered to an abdominal plane to numb the injection site, as well as for doctor or patient injection of medications or additional analgesic at a later time.

With reference to FIG. 2A, a detailed view of a device (300) for delivering analgesic to the abdominal wall of a patient, according to another embodiment of the invention, is illustrated. The device (300) includes a cannula stylet (304) having a sharp piercing tip (306) at a distal end thereof, and a reservoir (308) at a proximal end thereof. Similar to the above, the cannula stylet (304) has a hollow interior passageways that is in fluid communication with the reservoir (308). The reservoir (308) is configured to contain a predetermined amount of analgesic for delivery to a patient. As illustrated, the reservoir (308) includes a plunger (312) that can be actuated or depressed to dispense the contents of the reservoir (308) through the cannula stylet (304), as discussed above. The plunger (312) preferably includes an injection port (314) that allows for the selective injection of other compositions, such as analgesics, medications, etc., as indicated in prior embodiments. As further shown in FIG. 2A, the device (300) also includes a position stopper (310) defining a radially-extending flange that is mounted longitudinally along the cannula stylet (304). In an embodiment, the position stopper (310) is mounted in fixed position at a preset distance from the distal end of the cannula (304). In other embodiments, the cannula stylet (304) is slidable along the cannula stylet and selectively fixable at a desired location along the stylet (304). The purpose of the position stopper (310) is to prevent the cannula stylet (304) from penetrating too far into a patient and perforating the peritoneum. In particular, once the distal tip is positioned at the desired location for analgesic delivery, the position stopper (310) may be lowered along the cannula until it is in contact with the skin of the patient, preventing further inadvertent advancement of the distal tip into the body of the patient. In an embodiment, the device (300) may be utilized in connection with the device (200) described hereinbefore, wherein two such devices (300) form the dual-needle system described above. Moreover, it is contemplated that the position stopper (310) may be utilized in connection with any of the embodiments hereinbefore described.

Turning now to FIGS. 2B-2D, a guide device (350) that may form part of the systems hereinbefore described, is illustrated. As shown therein, the guide device (350) includes a hollow, inner cannula (352) having an injector inlet (354) at it proximal end, and an illumination element (356) at its distal end. In an embodiment, the inner cannula (352) may house a connector element (358) such as a fiber optic cable, electrical line, etc. for illuminating the illumination element (352). In an embodiment, the illumination element (356) may be a light-emitting diode (LED), although other types of light sources may also be utilized without departing from the broader aspects of the invention. As illustrated in FIG. 2B, in an embodiment, the proximal end of the cannula (352) may be bent at approximately 90 degrees so that the injector inlet (354) is oriented approximately 90 degrees from the longitudinal axis of the cannula (352).

As shown in FIGS. 2C and 2D, the guide device (350) is configured to be inserted into a hollow cannula stylet (360) having a sharp or pointed piercing tip (362). For example, in an embodiment, the hollow cannula stylet (360) may be the cannula stylet of the system/device of any of the above-disclosed embodiments. Importantly, the outer diameter of the inner cannula (352) and the outer diameter of the illumination element (356) is less than the inner diameter of the cannula stylet (360) which allows fluids such as an analgesic to pass out of the end of the cannula stylet (360), even when the guide device is slidably received therein.

With particular reference to FIG. 2C, in use, the guide device (350) is inserted into the cannula stylet (360) (e.g., the cannula stylets of any of the above-described embodiments) and advanced until the illumination element (356) is just shy of the distal end of the cannula stylet (360). The piercing tip (362) of the cannula stylet (360) is then used to pierce the skin of a patient, as the cannula stylet (360) is advanced into position. With reference to FIG. 2D, as the piercing tip (362) approaches the peritoneum, the light from the illumination element (356) will allow a user to detect the relative position of the piercing tip (362). At this point, the inner cannula (352) of the device (350) may advanced slightly further within the cannula stylet (360) until the illumination element (356) protrudes slightly beyond the piercing tip (362). Because the illumination element (356) has a blunt tip as compared to the piercing tip (362), inadvertent protrusion of the piercing tip (362) past the peritoneum is prevented. As further shown in FIG. 2D, in this position, an analgesic (364) can then be injected through the space between the inner cannula (352) and cannula stylet (360), and is permitted to leak out of the distal end of the cannula stylet (360), thereby delivering the analgesic to the desired site.

With reference to FIGS. 3A-3D various stylet guide devices for use with the needle devices disclosed above, for delivering an analgesic to the rectus sheath plane or transversus abdominus plane. With particular reference to FIG. 3A, a stylet guide device (400) for use with single needle devices (e.g., the device (300) of FIG. 2A) is shown. As illustrated therein, the stylet guide device (400) includes a guide template (402) in the form of a patch that may be placed over the skin (154) of a patient. In an embodiment, the guide template (402) is generally circular in shape, when viewed from above, although other configurations are possible without departing from the broader aspects of the invention. The guide template (402) includes a central, umbilicus guide hole (404) configured to facilitate alignment of the guide template (402) over the umbilicus, and a plurality of single needle guide holes (406) positioned at specific, predetermined, radially-spaced locations from the umbilicus guide hole (404). In an embodiment, the stylet guide device (400) may include a suction cup (408) for releasably securing the device (400) to the skin of the patient. In connection with this, the device (400) may include a suction valve (410) that may connect to a suction source for creating a vacuum beneath the suction cup (408) to affix the device (400) to the skin of the patient. In other embodiments, it is contemplated that an adhesive may be utilized to attached the device (400) to the skin of the patient. Other attachment means may also be utilized without departing from the broader aspects of the invention.

Figure 3B:
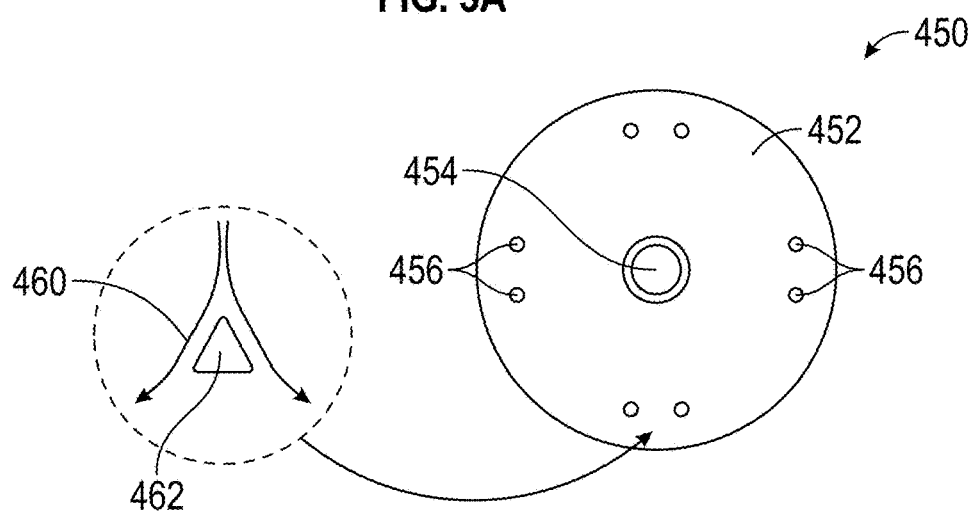
FIG. 3B is a simplified, top, plan view of a stylet guide device for use with, for example, the double stylet devices of FIGS. 1A, 1B and 1D.
Figure 3C:
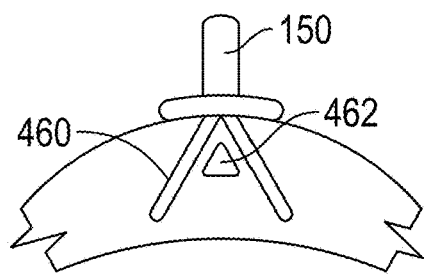
FIG. 3C is a simplified, cross-sectional view of the stylet guide device of FIG. 3B.
Figure 3D:
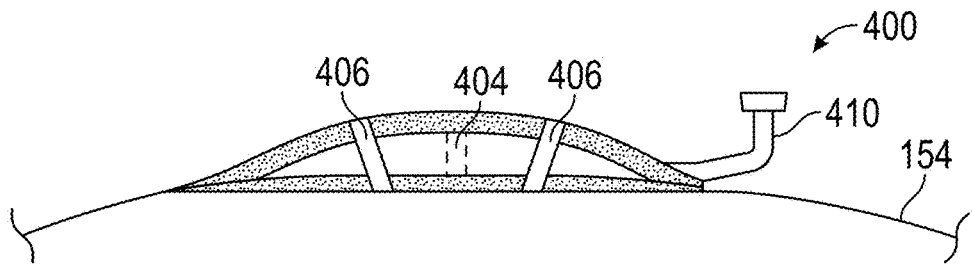
FIG. 3D is a simplified, cross-sectional view of the stylet guide device of FIG. 3A.

Turning to FIG. 3D, a cross-sectional view of the stylet guide device (400) is shown affixed to the skin (154) of a patient using suction. As shown therein, the holes (406) are angled inward toward the umbilicus guide hole (404). In this position, single needle devices such as those herein may be passed through the guide holes (406) and through the skin (154) of the patient to deliver analgesic to a desired side, as hereinbefore described.

With reference to FIGS. 3B and 3C, a stylet guide device (450) for use with double needle devices (e.g., the devices of FIG. 1A, 1B or 1D) is shown. The guide device (450) is substantially similar to guide device (400), and may be affixed to the skin of the patient using the same means. As shown in FIG. 3B, the device (450) similarly includes guide template (452) having a central, umbilicus guide hole (454) configured to facilitate alignment of the guide template (452) over the umbilicus. Rather than having single needle guide holes, however, the guide template (452) includes pairs of needle guide holes (456). Each hole within each pair of needle guide holes (456) is spaced approximately equidistant to the spacing between the distal ends of the cannula stylets of the needle device (e.g., distal ends (106) of cannula stylets (104) of device (100).

As further shown in FIG. 3B, the body of the guide device (450) defines stylet passages (460) in communication with the holes (456). In addition, the body of the guide device (450), between the holes that form each pair of holes (456) includes a fulcrum (462). Importantly, the fulcrum helps bend the cannula stylets (104) to their proper angle when inserted through the holes (456).

Figure 4:
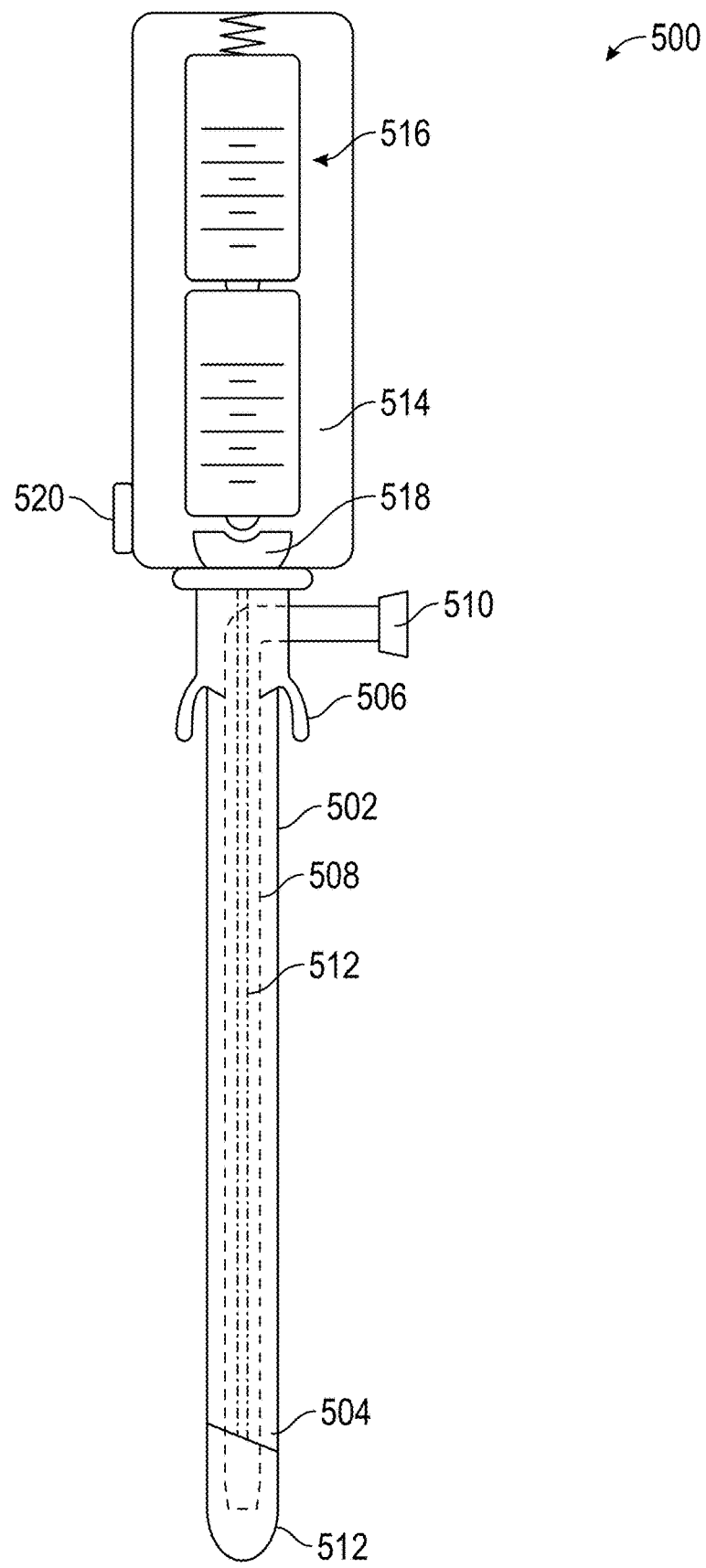
FIG. 4 is a side elevational view of a system/device for delivering analgesic to the abdominal wall, according to another embodiment of the invention.

Turning now to FIG. 4, a system/device (500) for delivering analgesic to the abdominal wall, according to another embodiment of the invention, is shown. The system (500) includes a hollow, outer cannula (502) having a proximal end and a sharp or pointed distal piercing tip (504). A proximal end of the cannula (502) may include a retainer clip (506) that holds the inner cannula, as discussed below. The system (500) also includes a hollow inner cannula (508) slidably receivable within the outer cannula (502). The inner cannula (508) has an injector inlet (510) at it proximal end, and an illumination element (512) at its distal end. Similar to the device (350) of FIG. 2B, the inner cannula (508) may house a connector element (512) such as a fiber optic cable, electrical line, etc. for transferring light to the distal tip and/or illuminating the illumination element (512). In an embodiment, the illumination element (512) may be a LED, although other types of light sources may also be utilized without departing from the broader aspects of the invention.

As illustrated, in an embodiment, the proximal end of the cannula (508) may be bent at approximately 90 degrees so that the injector inlet (510) is oriented approximately 90 degrees from the longitudinal axis of the cannula (508).

As further shown in FIG. 4, the system (500), at the proximal end of the cannula (502) includes a housing containing batteries (516) and a lens (518) adjacent to the proximal end of the cannula (502). In an embodiment, the system (500) may alternatively be powered by an external power source. In use, the device (500) may be inserted through the skin of a patient in the manner described above with prior embodiments. Once inserted into the patient, the battery (516) causes a circuit to close when button (520) on the housing (514) is depressed, causing the circular lens (518) to transfer the light source emitted by an LED to project itself to the distal end of the device.

In particular, as the piercing tip (504) approaches the peritoneum, the light from the illumination element (512) will allow a user to detect the relative position of the piercing tip (504). At this point, the inner cannula (508) of the device (500) may advanced slightly further within the outer cannula (502) until the illumination element (512) protrudes slightly beyond the piercing tip (504). Because the illumination element (512) has a blunt tip as compared to the piercing tip (504), inadvertent protrusion of the piercing tip (504) past the peritoneum is prevented. In this position, an analgesic can then be injected through port (510), where it passes through the space between the inner cannula (508) and outer cannula (502), and is permitted to leak out of the distal end of the device (500), thereby delivering the analgesic to the desired site.

Figure 5A:
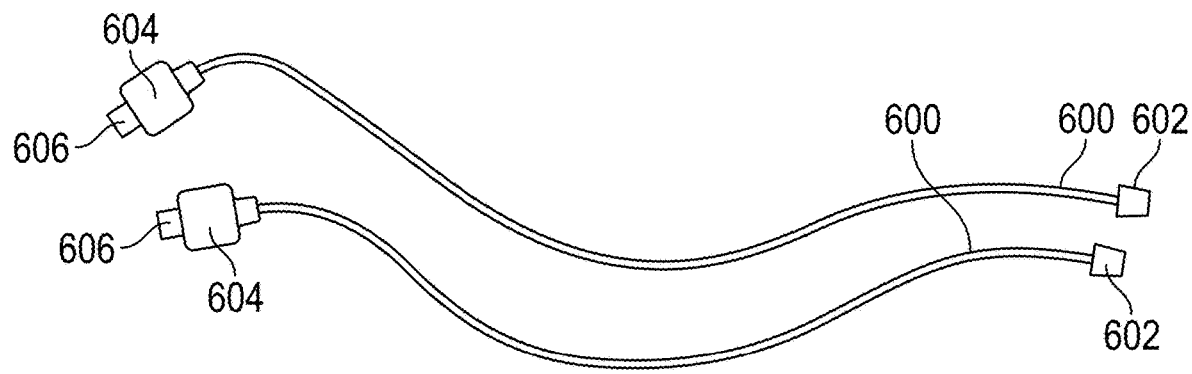
FIG. 5A is a perspective view of a pair of miniature catheter tubes for use with the devices disclosed herein.

FIG. 5A illustrates flexible catheter tubes (600) having connectors (602) at distal ends thereof, and reservoirs (604) with plungers (606) at proximal ends thereof. The connectors (602) are configured for connection to the ports in any of the devices previously disclosed (e.g., ports (102) of device (100)), for the injection of medication, analgesics, etc.

Figure 5B:
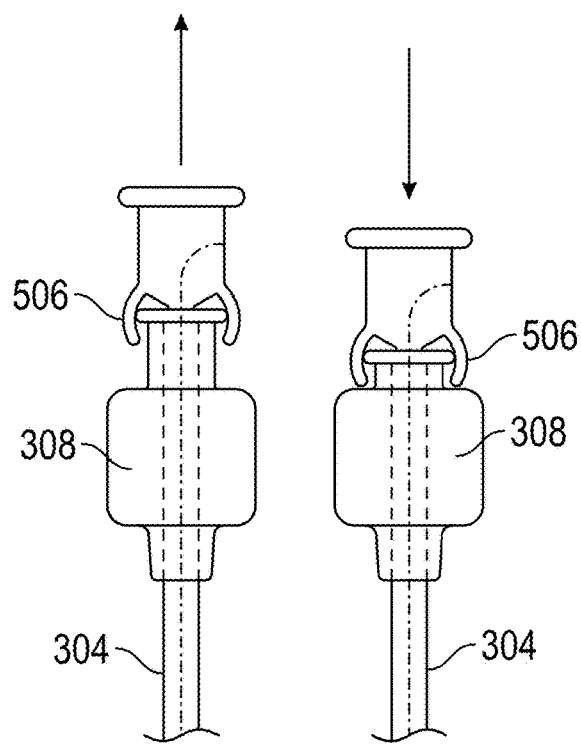
FIG. 5B presents a perspective view of a miniature catheter plunger device.

FIG. 5B presents detailed views showing how the retainer clip (506) may be used to connect the device (350) of FIG. 2B to, for example, the device (300) of FIG. 2A. As shown therein, the plunger may be depressed to deliver analgesic from reservoir (308), as disclosed above, and may be used with the catheter tubes of FIG. 5A.

Figure 5C:
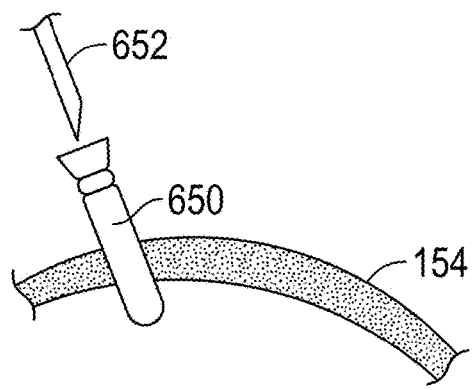
FIG. 5C is a perspective view of a stylet guide according to an embodiment of the invention.

Finally, FIG. 5C illustrates a stylet guide (650) that can be used to guide a piercing tip (652) of any of the above-disclosed devices through the skin (154) of a patient.

In an embodiment, a system for use in placing an abdominal wall block or infusion catheters is provided. The system includes a generally hollow needle having a proximal end and a pointed, distal tip, and an inner cannula slidably receivable within the hollow needle, the inner cannula having an illumination element on a distal end of the inner cannula. The inner cannula is movable between a retracted position where the illumination element is housed within the hollow needle, and an exposed position where the illumination element protrudes beyond the pointed, distal tip of the hollow needle. In an embodiment, the system further includes a reservoir at the proximal end of the hollow needle, the reservoir being in fluid communication with an interior of the hollow needle, wherein the reservoir is configured to contain an analgesic for delivery through the hollow needle. In an embodiment, the system also includes a plunger associated with the reservoir, the plunger being selectively actuatable to urge the analgesic from the reservoir and into the hollow needle. In an embodiment, the illumination element is a light-emitting diode. In an embodiment, the inner cannula houses a fiber optic cable for providing light to the illumination element. In an embodiment, the system may include a second generally hollow needle having a proximal end and a pointed, distal tip, a second reservoir at the proximal end of the hollow needle, the second reservoir being in fluid communication with an interior of the second hollow needle. The second reservoir is configured to contain an analgesic for delivery through the second hollow needle. The hollow needle and the second hollow needle may be connected at a hub. In an embodiment, the system additionally includes a first plunger associated with the reservoir, the first plunger being selectively actuatable to urge analgesic from the reservoir and into the hollow needle, and a second plunger associated with the second reservoir, the second plunger being selectively actuatable to urge analgesic from the second reservoir and into the second hollow needle. In an embodiment, the system includes a coupling member operatively connected to the first plunger and the second plunger, the coupling member being configured to distribute a dispensing force to both the first plunger and the second plunger to simultaneously deliver the analgesic from the first reservice and the second reservoir. In an embodiment, the system further includes a second inner cannula slidably received within the second hollow needle, the second inner cannula having a second illumination element on a distal end of the second inner cannula, wherein the second inner cannula is movable between a retracted position where the second illumination element is housed within the second hollow needle, and an exposed position where the second illumination element protrudes beyond the pointed, distal tip of the second hollow needle. In an embodiment, the system includes a guide template positionable on an abdomen of a patient, the guide template having a central hole for alignment with an umbilicus of the patient, and a plurality of single guide holes indicating an insertion location for the hollow needle. In an embodiment, the guide template includes a suction cup for affixing the guide template to the abdomen of the patient. In an embodiment, the plurality of single guide holes are spaced approximately equidistantly about a periphery of the guide template. In an embodiment, the guide template includes a needle passage used for directing the needle to a plane of a rectus sheath. In an embodiment, the system includes a guide template positionable on an abdomen of a patient, the guide template having a central hole for alignment with an umbilicus of the patient, and a plurality of guide hole pairs indicating an insertion location for the hollow needle and the second hollow needle. In an embodiment, the illumination element defines a blunt tip of the inner cannula.

In another embodiment, a method for placing an abdominal wall block or infusion catheter is provided. The method includes the steps of inserting an inner cannula having an illumination element on a distal end thereof within an outer cannula stylet, the outer cannula stylet having a piercing tip at a distal end thereof, piercing skin of a patient with the piercing tip, and advancing the inner cannula towards the distal end of the outer cannula stylet until the illumination element protrudes beyond the piercing tip of the outer cannula stylet to present a blunt surface to surrounding tissue of the patient. In an embodiment, the method may further include the step of depressing a plunger to dispense an analgesic from a reservoir into the outer cannula stylet. In an embodiment, the method may further include the steps of piercing the skin of the patient with a piercing tip of a second outer cannula stylet substantially simultaneously with the piercing of the skin with the piercing tip of the outer cannula stylet, and depressing a second plunger to dispense an analgesic from a second reservoir into the second outer cannula stylet. In an embodiment, the plunger and the second plunger are operatively connected to one another such that a single depressing force can be utilized to simultaneously dispense the analgesic from the reservoir and the second reservoir.

According to yet another embodiment of the invention, a device for use in placing an abdominal wall block or infusion catheters is provided. The device includes a first generally hollow needle having a proximal end and a pointed, distal tip, a second generally hollow needle having a proximal end and a pointed, distal tip, and a hub interconnecting the first needle with the second needle, wherein the first needle and the second needle are configured to deliver an analgesic to a patient. In an embodiment, the device further includes a first reservoir at the proximal end of the first needle, and a first plunger associated with the first reservoir, and a second reservoir at the proximal end of the second needle, and a second plunger associated with the second reservoir, wherein the first plunger and the second plunger are actuatable to dispense the analgesic from the first reservoir and the second reservoir, respectively.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

What is claimed is:

1. A method for placing an abdominal wall block or infusion catheter, comprising the steps of:
   aligning a central hole of a guide template with an umbilicus of a patient, the guide template placing a guide template having a plurality of pairs of guide holes;
   inserting a first outer cannula stylet and a second outer cannula stylet into one pair of the plurality of pairs of guide holes;
   piercing the skin of the patient with a piercing tip of the first outer cannula stylet and the second outer cannula stylet;
   inserting an inner cannula having an illumination element on a distal end thereof within the first outer cannula stylet; and
   advancing the inner cannula towards the distal end of the first outer cannula stylet until the illumination element protrudes beyond the piercing tip of the first outer cannula stylet to present a blunt surface to surrounding tissue of the patient.

2. The method according to claim 1, further comprising the step of:
   depressing a plunger to dispense an analgesic from a reservoir into the first outer cannula stylet.

3. The method according to claim 2, further comprising the step of:
   depressing a second plunger to dispense an analgesic from a second reservoir into the second outer cannula stylet.

4. The method according to claim 3, wherein:
   the plunger and the second plunger are operatively connected to one another such that a single depressing force can be utilized to simultaneously dispense the analgesic from the reservoir and the second reservoir.

5. A system for use in placing an abdominal wall block or infusion catheters, comprising:
   a first generally hollow needle having a proximal end and a pointed, distal tip, and a first reservoir at the proximal end of the first hollow needle, the first reservoir being in fluid communication with an interior of the first hollow needle, wherein the first reservoir is configured to contain an analgesic for delivery through the first hollow needle;
   a second generally hollow needle having a proximal end and a pointed, distal tip, a second reservoir at the proximal end of the second hollow needle, the second reservoir being in fluid communication with an interior of the second hollow needle, wherein the second reservoir is configured to contain an analgesic for delivery through the second hollow needle;
   a first plunger associated with the first reservoir, the first plunger being selectively actuatable to urge analgesic from the first reservoir and into the first hollow needle;
   a second plunger associated with the second reservoir, the second plunger being selectively actuatable to urge analgesic from the second reservoir and into the second hollow needle;
   a coupling member operatively connected to the first plunger and the second plunger, the coupling member being configured to distribute a dispensing force to both the first plunger and the second plunger to simultaneously deliver the analgesic from the first reservoir and the second reservoir;
   a guide template positionable on an abdomen of a patient, the guide template having a central hole for alignment with an umbilicus of the patient, and a plurality of guide holes indicating an insertion location for the first hollow needle and the second hollow needle;
   wherein the first hollow needle and the second hollow needle are connected at a hub;
   wherein the coupling member is removable from the first plunger and the second plunger to allow for dispensing of the first reservoir and the second reservoir independently of one another; and
   wherein the plurality of guide holes are a plurality of pairs of guide holes for receiving the first hollow needle and the second hollow needle.

6. A system for use in placing an abdominal wall block or infusion catheters, comprising:
   a first generally hollow needle having a proximal end and a pointed, distal tip, and a first reservoir at the proximal end of the first hollow needle, the first reservoir being in fluid communication with an interior of the first hollow needle, wherein the first reservoir is configured to contain an analgesic for delivery through the first hollow needle;
   a second generally hollow needle having a proximal end and a pointed, distal tip, a second reservoir at the proximal end of the second hollow needle, the second reservoir being in fluid communication with an interior of the second hollow needle, wherein the second reservoir is configured to contain an analgesic for delivery through the second hollow needle;
   a first plunger associated with the first reservoir, the first plunger being selectively actuatable to urge analgesic from the first reservoir and into the first hollow needle;

a second plunger associated with the second reservoir, the second plunger being selectively actuatable to urge analgesic from the second reservoir and into the second hollow needle;

a coupling member operatively connected to the first plunger and the second plunger, the coupling member being configured to distribute a dispensing force to both the first plunger and the second plunger to simultaneously deliver the analgesic from the first reservoir and the second reservoir;

a guide template positionable on an abdomen of a patient, the guide template having a central hole for alignment with an umbilicus of the patient, and a plurality of guide holes indicating an insertion location for the first hollow needle and the second hollow needle;

wherein the first hollow needle and the second hollow needle are connected at a hub;

wherein the coupling member is removable from the first plunger and the second plunger to allow for dispensing of the first reservoir and the second reservoir independently of one another; and wherein the guide template includes a fulcrum in between each holes of each pair of guide holes, the fulcrum being configured to help bend the first hollow needle and the second hollow needle when inserted through a pair of guide holes of the plurality of pairs of guide holes.

7. A device for use in placing an abdominal wall block or infusion catheters, comprising:

a first generally hollow needle having a proximal end and a pointed, distal tip;

a second generally hollow needle having a proximal end and a pointed, distal tip;

a hub interconnecting the first needle with the second needle;

a guide template positionable on an abdomen of a patient, the guide template having a central hole for alignment with an umbilicus of the patient, and a plurality of guide holes indicating an insertion location for the first hollow needle and the second hollow needle;

wherein the first needle and the second needle are configured to deliver an analgesic to a patient;

wherein the plurality of guide holes are a plurality of pairs of guide holes for receiving the first hollow needle and the second hollow needle.

8. The device of claim 7, further comprising:

a first reservoir at the proximal end of the first needle, and a first plunger associated with the first reservoir; and a second reservoir at the proximal end of the second needle, and a second plunger associated with the second reservoir; and a coupling member operatively connected to the first plunger and the second plunger, the coupling member being configured to distribute a dispensing force to both the first plunger and the second plunger to simultaneously deliver the analgesic from the first reservoir and the second reservoir;

wherein the coupling member is removable from the first plunger and the second plunger to allow for dispensing of the first reservoir and the second reservoir independently of one another.

9. The system of claim 7, wherein:

the guide template includes a fulcrum in between each holes of each pair of guide holes, the fulcrum being configured to help bend the first hollow needle and the second hollow needle when inserted through a pair of guide holes of the plurality of pairs of guide holes.

* * * * *